United States Patent [19]
Anstaett et al.

[11] Patent Number: 5,755,807
[45] Date of Patent: May 26, 1998

[54] IMPLANT MODULE UNIT AND ROTATING SEAL FOR PROSTHETIC JOINT

[75] Inventors: Gene Anstaett, Alabaster; Michael Robert Klardie, Birmingham; Aubrey Clinton Folsom, Pelham; Peter J. Czuwala, Birmingham, all of Ala.

[73] Assignee: Folsom Metal Products, Pelham, Ala.

[21] Appl. No.: 666,890

[22] Filed: Jun. 17, 1996

[51] Int. Cl.$^6$ .......................................................... A61F 2/36
[52] U.S. Cl. .................... 623/23; 623/18; 623/19; 623/22
[58] Field of Search ............................ 623/18–23; 606/89

[56] References Cited

U.S. PATENT DOCUMENTS

| | | |
|---|---|---|
| 3,648,294 | 3/1972 | Shahrestani . |
| 3,683,421 | 8/1972 | Martinie . |
| 3,830,083 | 8/1974 | Hadick et al. . |
| 3,848,276 | 11/1974 | Martinez . |
| 3,864,758 | 2/1975 | Yakich . |
| 3,869,730 | 3/1975 | Skobel . |
| 4,571,749 | 2/1986 | Fischell ........................ 623/14 |
| 4,676,798 | 6/1987 | Noiles . |
| 4,731,088 | 3/1988 | Collier . |
| 4,822,368 | 4/1989 | Collier . |
| 4,854,428 | 8/1989 | Horvath . |
| 5,002,581 | 3/1991 | Paxson et al. . |
| 5,040,606 | 8/1991 | Hopper ........................ 166/332 |
| 5,389,107 | 2/1995 | Nassar et al. .................. 623/22 |
| 5,514,182 | 5/1996 | Shea . |

Primary Examiner—Michael J. Milano
Assistant Examiner—Tram Anh T. Nguyen
Attorney, Agent, or Firm—Veal & Associates

[57] ABSTRACT

An implantable module for use with a prosthetic joint that utilizes a bellows and a rotating seal for encapsulating the articulating members of the implant. This invention is comprised of flexible metallic bellows which serve the same function as the presently used boot, which includes containing a lubricant to decrease the wear to the articulating surfaces and preventing the lubricant or wear debris from escaping into the surrounding tissues. The implant module has the novel feature of maintaining the articulating bearing surfaces in proper alignment by utilizing a spring force from the metallic bellows to augment the function of the tendons, ligaments, and muscles that have been surgically traumatized and to prevent exposure of the articulating surfaces to excessive expansion, compression, or rotational forces. Furthermore, a thrust bearing with rotating seal is located between the flexible bellows and the neck of the implant freeing the bellows from rotational cycles, thus increasing the life of the bellows. The thrust bearing transfers the spring force from the metallic bellows to the permanent implant and prevents axial movement of the rotating seal along the neck. The thrust bearing with rotating seal can also be used to enhance the performance and longevity of non-metallic flexible members. The implant module includes the metallic bellows, the thrust bearing with rotating seal and the enclosed lubricated articulating assembly. If necessary, the implant module may be surgically removed and replaced by a new implant module without disturbing the integrity of other implantable components that are affixed to bone.

14 Claims, 3 Drawing Sheets

IMPLANT MODULE UNIT AND ROTATING SEAL FOR PROSTHETIC JOINT

FIELD OF THE INVENTION

The present invention relates generally to the field of surgery and has particular application to a total prosthetic joint implant and the implantation thereof.

BACKGROUND OF THE INVENTION

This invention relates broadly to a means for transferring forces imposed on load bearing portions of artificial joints to bone in humans and animals. The present invention is applicable for surgical procedures that utilize implantable prosthetic devices to reconstruct a joint within a human or animal. While the present invention is applicable in various implant types, it will be described herein, for purposes of example only, as being specifically adapted for use in a total hip joint prosthesis, such as the Charnley type hip implant. Although hip prostheses will be used for illustrative purposes only, features of the invention will be stated in a generic form so that they are applicable to all joint prostheses and to the geometric and biomedical properties of all animal and human joints.

The natural human hip joint is considered a relatively frictionless ball and socket joint that is enclosed by a soft tissue capsule. The ball-like head of the femur rotates within the socket or acetabulum situated in the pelvis. The soft tissue capsule is comprised of ligaments; the ilio-femoral, ischio-femoral and pubo-femoral ligaments being external to the joint while the ligamentum teres is an internal ligament. A primary function of these ligaments is to retain the femur lightly in the acetabulum, prevent extension of the femur much beyond the straight position, and limit the extent of abduction/adduction and movements of rotation. The femoral head and acetabulum are both lined with articular cartilage. The cartilage acts as a bearing material while the synovial fluid, contained within and produced by the synovial membrane of the ligamentous capsule, acts as a lubricant for the hip joint.

When the natural hip joint displays an appropriate anomaly, sufficient damage or diseased state, it is the practice to replace the femoral head with a prosthesis including a ball member attached to the femur by a neck and stem which fits into the medullary canal, and to fit a corresponding artificial socket member into the acetabulum, which may be suitably enlarged for the purpose. The present invention may be utilized in a total hip joint reconstructive procedure in which the ligamentous capsule is usually resected. When the ligaments of the natural joint are resected during the reconstructive procedure, the artificial joint is inherently less stable and subject to dislocation. In addition, the lubricating synovial fluid is not produced when the capsule with synovial membrane is removed.

Total joint arthroplasty, the reconstruction of a joint and its surrounding tissues, is a procedure commonly performed to correct defective joints as a consequence of trauma, disease or congenital anomalies. By necessity, this surgical procedure uses biocompatible materials that may include metals, plastics, ceramics, or the like to achieve a functional reconstruction. The implants typically attach metal components to the bones of a diarthrodial joint and are coupled utilizing an articulating mechanism to transfer forces between the femoral and acetabular metallic components. The coupling may be comprised of metallic, ceramic, or plastic articulation members, including, but not limited to, such an articulating bearing made of metal in contact with an ultra high molecular weight polyethylene member. This coupling should maintain proper alignment of the articulation members, allow near natural movement of the prosthetic joint and provide an adequate transfer of load between the prosthetic members.

Total joint replacement implants have evolved into modular components to allow surgeons greater intra-operative flexibility to a patients' anatomic variations. These modular components are rigidly affixed to the bone, forming a joint with an articulating assembly. An example of a modular joint implant is illustrated in U.S. Pat. No. 5,002,581.

The predominate mode of long-term prosthetic failure of total hip procedures is a consequence of particulate matter according to a 1994 National Institutes of Health Consensus Statement. The particulate matter has been shown to consist of wear debris generated from the prosthetic articulation. The high contact stress at the articulating bearing surfaces generates wear debris that is accelerated as a result of either poor or non-existent lubrication. The wear debris generated is typically comprised of sub-micron particles from both the acetabular and femoral components. Polymeric wear particles may form a thin transfer film layer of polymer on the metallic surface resulting in adhesive wearing of the plastic surface in joint implants utilizing a metal to plastic articulating bearing. The debris migrates from the artificial joint into the surrounding tissue and induces histaminic reactions that may lead to tissue inflammation, pain, and loosening of the implant from the surrounding bone. Excessive wear from the articulating surfaces will usually require the replacement of one or more of the prosthetic components due to bone resorption around the metallic bony component(s) [i.e., osteolysis].

Some previous joint implants were designed to isolate the wear particulate from the surrounding tissue by enclosing the articulation with an impermeable flexible member, e.g. U.S. Pat. No. 4,731,088. The flexible members were made from woven polymers, polyethylene, plastics, reinforced fabrics or an elastomeric material such as silicon rubber. The flexible members may enclose a lubricating fluid such as pure silicon oil, distilled water, collagen solution or mineral oil. These designs allow lubricants superior to non-synovial body fluids to be used to prolong the life of the implant while preventing wear debris from seeping into the surrounding tissues.

A problem with the polymeric flexible implant designs is that both ends of the flexible member are rigidly affixed. Rigid fixation exposes the member to both rotational and lateral translational forces leading to stress fatigue with eventual deterioration of the flexible member. Further, degradation of the flexible members has been observed at the attachment points due to changes in material properties of polymers under cyclic loading and cold flow of the material. In addition, the micron and sub-micron particles of wear debris become entrapped within the pores causing further deterioration and crack propagation of the elastomeric material(s).

There exists an increased potential for artificial joint dislocation when total joint prostheses are implanted into a patient with ligamentous laxity. Some total joint implant devices have been designed so that the artificial femoral head is constrained within the artificial acetabulum in an attempt to correct the dislocation problem; however, these constrained devices transfer greater forces to the acetabular components due to a lever effect that would normally cause dislocation. Therefore, higher stresses occur at the bone/acetabular component interface that results in loosening of the acetabular component. An example of a constrained device is shown in U.S. Pat. No. 4,676,798.

Many improvements have been made in the field of prosthetic joint implants, however, further development is necessary to correct shortcomings that exist with current implant designs. For example, current total joint replacements rely on tendons, ligaments, and muscle forces acting across the joint to hold the articulating members in proper alignment. Soft tissues surrounding the joint may be transected, resected, reflected, retracted, distracted, sutured and otherwise subjected to surgical trauma by necessity of the total joint arthroplasty procedure. This compromises the joint's stability and increases the potential of the joint to dislocate. The flexible members presently used in joint implants are not designed to provide suitable forces to keep the articulating surfaces of the implant in contact. Moreover, these non-metallic flexible members are not designed to provide rotational stability to the joint. Therefore, the implant is still susceptible to misalignment and undue wear resulting from compression, expansion, and rotational forces on the articulating members of the joint implant.

The present invention is an implant module unit that incorporates flexible metal bellows and a thrust bearing with rotating seal. The implant module unit is designed to reduce the wear at the articulating bearing surfaces, and thus, lengthen the life of the prosthesis. The metallic flexible bellows, having a spring force, will reinforce the coupling between the articulating members and provide an implant with greater integrity. Additionally, the metallic bellows are mounted to the articulating members in such a manner that the bellows are not subject to the rotational forces that will lead to the deterioration of the bellows.

SUMMARY OF THE PRESENT INVENTION

It is an object of the present invention to provide an implantable module unit for use with a prosthetic joint that utilizes a bellows and a rotating seal for encapsulating the articulating members of an implant.

It is a further object of the present invention to provide an implant module unit that contains a lubricant which lowers the coefficient of friction between the articulating surfaces and thus reduces wear of the joint.

It is still a further object of the present invention to provide an implant module unit that will isolate the wear particles from interacting with the surrounding tissues.

It is another object of the present invention to provide a metallic bellows with a greatly increased fatigue life over previous polymeric membranes including, but not limited to, rubber membranes, polyethylene membranes, reinforced fabric membranes, and membranes made from woven polymers.

It is yet another object of the present invention to provide a thrust bearing with a rotating seal between the flexible bellows and one of the joint members to isolate the bellows from rotational cycles, thus increasing the life of the bellows.

It is still a further object of the present invention to provide a thrust bearing with a rotating seal on one of the joint members to prevent axial movement of the rotating seal between the joint member and the distal end of the bellows.

It is an additional object of the present invention to provide metallic flexible bellows which augment the function of surgically traumatized tendons, ligaments, and muscles. The metallic bellows will have sufficient spring force to enhance the integrity of the joint and maintain contact between the articulating surfaces.

It is a further object of the invention to provide a removable module unit which includes the flexible bellows, the thrust bearing with rotating seal, and the enclosed lubricated articulating assembly, thus allowing the module unit to be surgically removed and replaced by a new module unit without disturbing the integrity of the permanent implants in the bones.

These and other objects of the present invention are accomplished through the use of an implant module unit and rotating seal for prosthetic joint. The improved joint implant is the type which utilizes a boot for encapsulating the articulating members of the implant. The flexible metallic bellows has a similar function as the presently used boot. The bellows will contain a lubricant to decrease the wear between the articulating surfaces and prevent the lubricant or wear debris from escaping into the surrounding tissues. In addition, the improved bellows has the novel feature of maintaining the articulating surfaces of the implant in proper alignment by employing the spring force from the metallic bellows. This spring force assists the coupling to maintain proper compression, expansion or rotational forces, thus augmenting the function of surgically traumatized tendons, ligaments, and muscles. The implant utilizes a rotating seal joint between the flexible bellows and one of the implant members to isolate the bellows from rotational cycles, thus increasing the life of the bellows. Additionally, a thrust bearing is located on an implant member to transfer the spring force from the metallic bellows to the permanent implant and to prevent axial movement of the rotating seal between the permanent implant and the distal end of the bellows. The implant module unit consists of the metallic bellows, thrust bearing with rotating seal, and the enclosed lubricated articulating assembly. The implant module unit may be surgically removed and replaced by a new module unit without disturbing the integrity of the permanent implants in the bones.

These and other objects and advantages of the invention will become apparent from the following detailed description of the preferred embodiment of the invention.

BRIEF DESCRIPTION OF THE DRAWINGS

A prosthetic joint implant embodying features of the invention is described in the accompanying drawings which form a portion of this disclosure and wherein.

DETAILED DESCRIPTION OF THE PREFERRED EMBODIMENT

The present invention may be utilized to replace synovial joints, ball and socket joints, hinge joints, and condylar joints (i.e. hip, knee, elbow, shoulder, wrist, etc.) in humans and animals. While the present invention is applicable in various types of implants, it will be described herein, for purposes of illustration only, as being adapted for use in a total hip prosthesis, such as the Charnley type hip implant.

Figure 1:
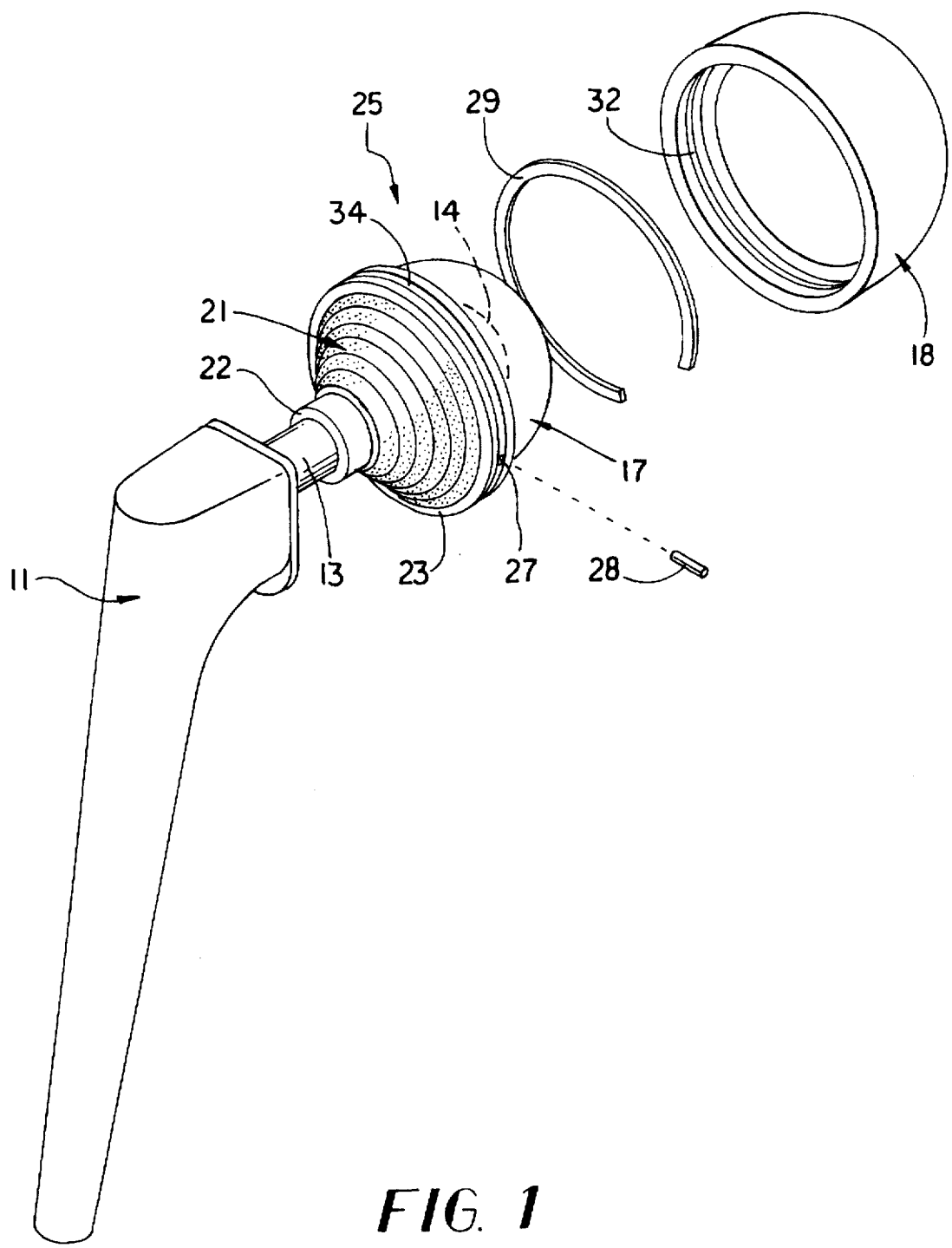
FIG. 1 is an exploded perspective view of the present invention as used in a ball and socket type joint implant.
Figure 2:
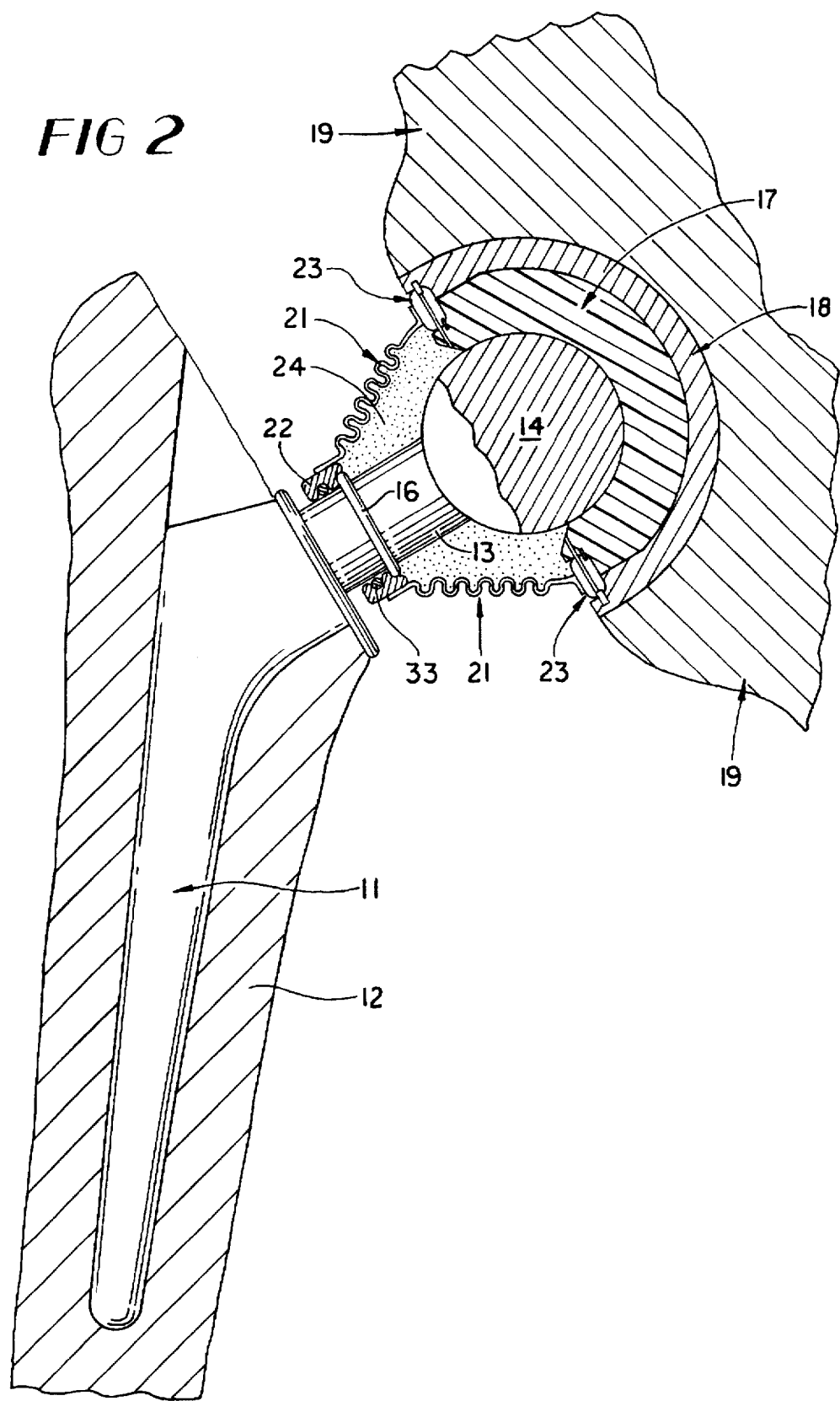
FIG. 2 is a sectional view of the present invention as used in a ball and socket type joint implant.
Figure 3:
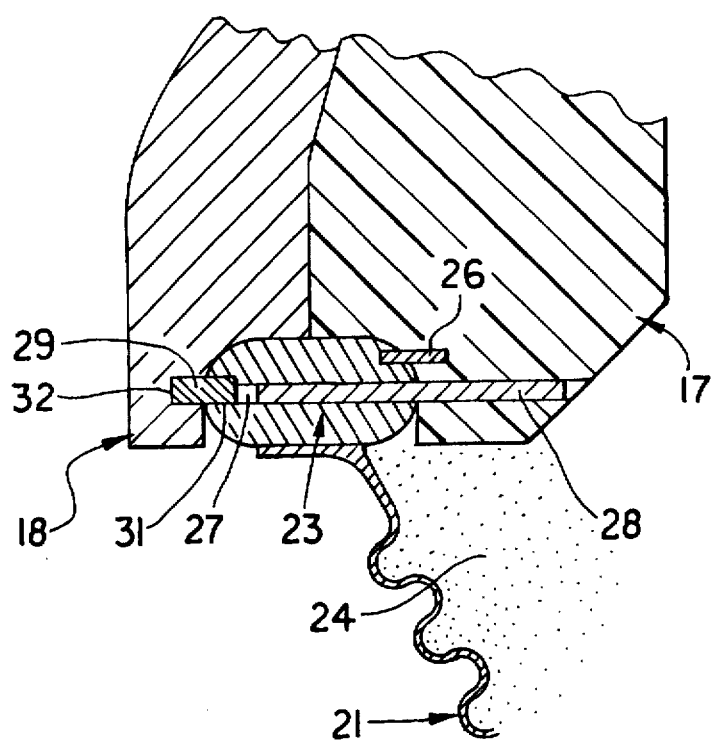
FIG. 3 is an enlarged sectional view of the point of attachment of the modular unit to the permanent implant in the ball and socket type joint implant.

In order to understand the features of the present invention, refer to the accompanying drawings wherein the total hip implant, according to the embodiment shown in FIGS. 1–3, is comprised of a femoral component 11 implanted into the proximal bone of the femur 12. Femoral component 11 is typically comprised of a metal, such as titanium, titanium alloy or an alloy of cobalt-chromium, and is designed to be a permanent implant in the body such that replacement should not be necessary. Attached to the proximal end of the femoral component 11 is a femoral neck 13 and head 14. Femoral neck 13 has formed thereon a thrust bearing 16. Femoral neck 13 and thrust bearing 16 are typically comprised of titanium or alloys of titanium, cobalt, steel, or surface modified versions of these materials. Femoral head 14 is preferably comprised of a ceramic material, although it can also be comprised of various metals including that of titanium or alloys of titanium, cobalt, steel, or surface modified versions of these materials. Femoral head 14 fits into a cavity formed within an acetabular cup 17. The cup is typically comprised of a high density plastic such as ultra high molecular weight polyethylene, or metal such as titanium or alloys of titanium, cobalt, steel, or surface modified versions of these materials or any combination thereof. This acetabular cup 17 is attached to an acetabular shell 18, which may be osseointegrated or rigidly affixed to the pelvis 19. The acetabular shell 18 is typically comprised of a metal, such as titanium or alloys of titanium, cobalt, steel, or surface modified versions of these materials, and is designed for permanent implantation.

The acetabular cup 17 and femoral head 14 comprise the articulating surfaces which must be replaced if they become worn or misaligned. Encapsulating the articulating surfaces are metallic bellows 21, preferably comprised of titanium or alloys of titanium, cobalt, steel, or surface modified versions of these materials, and can consist of various geometries. Bellows 21 are attached at one end to a rotating seal 22, which is mounted about femoral neck 13 adjacent to thrust bearing 16, and at the opposite end to a retaining ring 23, comprised of titanium or alloys of titanium, cobalt, steel, or surface modified versions of these materials. The rotating seal 22 contains one or more O-rings 33, which prevents an exchange of fluid yet allows rotational movement of the femoral head 14 relative to the acetabular cup 17. Retaining ring 23, shown enlarged in FIG. 3, is attached to acetabular cup 17 and acetabular shell 18 such that a cavity 24 is formed encapsulating the articulating surfaces. Cavity 24 is filled with a bio-tolerant lubricant, preferably one comprised of pure silicon oil, distilled water, collagen solution, mineral oil or natural organic product extracts in solution. Bellows 21 are impermeable to fluids to prevent any exchange between body fluids and lubricant.

Femoral neck 13, femoral head 14, thrust bearing 16, acetabular cup 17, rotating seal 22 with O-ring(s) 33, retaining ring 23, and metallic bellows 21 form an implant module 25 which is pre-assembled as a unit before implantation. Thus, if the articulating surface become worn and need to be replaced, only the implant module need be removed and conveniently substituted with a new implant module. Implant module 25 is attached to femoral component 11 by femoral neck 13 and to acetabular shell 18 by retaining ring 23. Retaining ring 23 has a circumferential clip 26 thereabout for permanent attachment to acetabular cup 17. Clip 26 is preferably comprised of titanium or alloys of titanium, cobalt, steel, or surface modified versions of these materials. Retaining ring 23 has at least one portal 27 therethrough for introduction of a lubricant into cavity 24 after the implant module 25 has been assembled. Portal 27 is sealed with a plug 28 after cavity 24 has been filled with the lubricant and prior to implantation into a host. Plug 28 provides additional support once inserted by securing retaining ring 23 to acetabular cup 17. Alternatively, the portal may be located through the wall of the bellows (not shown) to allow the lubricant to be monitored for wear debris or seepage, or exchanged if necessary. Retaining ring 23 is held within acetabular shell 18 by a snap spring 29 which is placed in a circumferential groove 31 in retaining ring 23. The acetabular shell 18 has a complementary circumferential groove 32 therein such that snap spring 29 may be placed within complementary grooves 31 and 32 to secure the implant module 25 to acetabular shell 18.

The metallic bellows overcome problems found in prior art. The bellows contain the lubricant and prevent either lubricant or wear debris from escaping into the surrounding tissues. In addition, the metallic bellows have a much longer life than their elastomeric counterparts. This reduces the need for implant replacement from lubricant or debris seepage into the surrounding tissues resulting from a breach in the membrane of the polymeric bellows. The spring effect of the metallic bellows adds support to the implant by holding the articulating surfaces in contact. For example, the metallic bellows hold the femoral head within the acetabular cup in the hip type joint implant. Thus, the metallic bellows provide functional assistance for recuperating tendons, ligaments, and muscles that are commonly surgically traumatized during the arthroplasty procedure. This functional assistance provided by these metallic bellows is not found in the designs of prior art for polymeric bellows. The metallic bellows reduce the likelihood of wear caused by malalignment of the articulating surfaces and reduces the likelihood of an articular dislocation.

The rotating seal joint isolates the bellows from rotational cycles, thus increasing the life of the bellows. This is especially useful when the boot is comprised of an elastomeric material which is much more susceptible to degradation than the metallic boot. Additionally, the thrust bearing 16 surface allows the spring force pressure from the metallic bellows to be transferred to the permanent implant and prevents axial movement of the rotary seal 22 along femoral stem 13 toward femoral head 14.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. An implant for use in joint replacement surgery comprising an articulation assembly having at least two articulating surfaces, and flexible metallic bellows for maintaining said articulating surfaces in proper alignment by utilizing a spring force from said metallic bellows to prevent said articulating surfaces from being exposed to excessive compression or expansion forces, wherein said articulation assembly comprises:

(a) a first member having a first portion rigidly affixed to a first bone and a second portion having an articulating surface;

(b) a second member having a first portion rigidly affixed to a second bone and a second portion having an articulating surface; and (c) a thrust bearing formed on said second portion of said first member to transfer said spring force from said metallic bellows to said articulation assembly.

2. An implant as defined in claim 1, further comprising at least one rotating seal for attaching said metallic bellows to said second portion of said first member to prevent said metallic bellows from being exposed to rotational forces.

3. An implant as defined in claim 2, wherein said rotating seal is mounted adjacent said thrust bearing to prevent axial movement of said rotary seal between said first portion of said first member and said articulating surface of said second portion of said first member.

4. An implant for use in joint replacement surgery, comprising:
   (a) a first member having a first portion rigidly affixed to a first bone and a second portion having an articulating surface;
   (b) a second member having a first portion rigidly affixed to a second bone and a second portion having an articulating surface;
   (c) a third member rotatably mounted about said first member;
   (d) flexible metallic bellows sealably encapsulating said articulating surfaces of said first and second members wherein a cavity formed by said bellows is filled with a lubricant for reducing frictional wear between said articulating surfaces, said bellows being rigidly affixed at one end to said second member and rigidly affixed at an opposite end to said third member such that said first member can rotate within said third member without imparting rotational forces to said bellows, said bellows having sufficient spring force to augment the function of surgically traumatized tendons, ligaments, and muscles to maintain said articulating surfaces in proper alignment and prevent said articulating surfaces from being exposed to excessive compression or expansion forces; and
   (e) a thrust bearing formed on said second portion of said first member to transfer spring force from said metallic bellows to said first member.

5. An improved implant as defined in claim 4, wherein said third member is a rotating seal.

6. An improved implant as defined in claim 5, wherein said rotating seal is mounted adjacent said thrust bearing to prevent axial movement of said rotating seal between said first portion of said first member and said articulating surface of said second portion of said first member.

7. An implant for use in joint replacement surgery, comprising:
   (a) a first member having a first portion rigidly affixed to a first bone and a second portion having an articulating surface;
   (b) a second member having a first portion rigidly affixed to a second bone and a second portion having an articulating surface;
   (c) a third member rotatably mounted about said first member;
   (d) flexible elastomeric bellows sealably encapsulating said articulating surfaces of said first and second members wherein a cavity formed by said bellows is filled with a lubricant for reducing frictional wear between said articulating surfaces, said bellows being rigidly affixed at one end to said second member and rigidly affixed at an opposite end to said third member such that said first member can rotate within said third member without imparting rotational forces to said bellows; and
   (e) a thrust bearing surface formed on said second portion of said first member.

8. An improved implant as defined in claim 7, wherein said third member is a rotating seal.

9. An improved implant as defined in claim 8, wherein said rotating seal is mounted adjacent said thrust bearing to prevent axial movement of said rotating seal between said first portion of said first member and said articulating surface of said second portion of said first member.

10. An implant for use in joint replacement surgery, comprising in combination:
    (a) a first member rigidly affixed to a first bone;
    (b) a second member having a first and second end, wherein said first end is mounted to said first member and said second end has an articulating surface;
    (c) a third member rigidly affixed to a second bone;
    (d) a fourth member having a first and second end, wherein said first end is mounted to said third member and said second end has an articulating surface in contact with said articulating surface of said second member;
    (e) a seal rotatably mounted about said second member;
    (f) a flexible boot sealably encapsulating said articulating surfaces of said second and said fourth members wherein a cavity formed by said boot is filled with a lubricant for reducing frictional wear between said articulating surfaces, said boot being rigidly affixed at a first end to said fourth member and rigidly affixed at an opposite end to said rotatable seal such that said second member can rotate within said seal without imparting rotational forces to said boot; and
    (g) connecting means mounted to said first end of said fourth member for connecting said first end of said bellows to said first end of said fourth member and for connecting said first end of said fourth member to said third member, wherein said connecting means comprises in combination: a circumferential clip for rigidly affixing said connecting means to said first end of said fourth member; a removable circumferential snap spring for affixing said connecting means to said third member; and a sealable portal through said connecting means for delivering a lubricant into said cavity.

11. An implant for use in joint replacement surgery, comprising in combination:
    (a) a first member rigidly affixed to a first bone;
    (b) a second member having a first and second end, wherein said first end is mounted to said first member and said second end has an articulating surface;
    (c) a third member rigidly affixed to a second bone;
    (d) a fourth member having a first and second end, wherein said first end is mounted to said third member and said second end has an articulating surface in contact with said articulating surface of said second member;
    (e) a seal rotatably mounted about said second member;
    (f) flexible metallic bellows sealably encapsulating said articulating surfaces of said second and said fourth members wherein a cavity formed by said bellows is filled with a lubricant for reducing frictional wear between said articulating surfaces, said bellows being rigidly affixed at a first end to said fourth member and rigidly affixed at an opposite end to said rotatable seal such that said second member can rotate within said seal without imparting rotational forces to said bellows, said bellows having sufficient spring force to augment the function of surgically traumatized tendons, ligaments, and muscles to maintain said articulating surfaces in proper alignment and prevent said articulating surfaces from being exposed to excessive compression or expansion forces; and
    (g) a thrust bearing surface formed on said second member between said first end and said second end to transfer spring force from said metallic bellows to said second member.

12. An implant as defined in claim 11, wherein said rotatable seal is mounted adjacent said thrust bearing to prevent axial movement of said rotatable seal between said first end of said second member and said second end of said second member.

13. An implant for use in joint replacement surgery, comprising in combination:

(a) a first member rigidly affixed to a first bone;

(b) a second member having a first and second end, wherein said first end is mounted to said first member and said second end has an articulating surface;

(c) a third member rigidly affixed to a second bone;

(d) a fourth member having a first and second end, wherein said first end is mounted to said third member and said second end has an articulating surface in contact with said articulating surface of said second member;

(e) a seal rotatably mounted about said second member;

(f) flexible elastomeric bellows sealably encapsulating said articulating surfaces of said second and said fourth members wherein a cavity formed by said bellows is filled with a lubricant for reducing frictional wear between said articulating surfaces, said bellows being rigidly affixed at a first end to said fourth member and rigidly affixed at an opposite end to said rotatable seal such that said second member can rotate within said seal without imparting rotational forces to said bellows; and (g) a thrust bearing surface formed on said second member between said first end and said second end.

14. An improved implant as defined in claim 13, wherein said rotatable seal is mounted adjacent said thrust bearing to prevent axial movement of said rotatable seal between said first end of said second member and said second end of said second member.

* * * * *